United States Patent [19]

Karrer

[11] 4,141,921
[45] Feb. 27, 1979

[54] PHENOXYPHENYL- AND PHENOXYBENZYL-ALKYNYL ETHERS

[75] Inventor: Friedrich Karrer, Basel, Switzerland

[73] Assignee: Ciba-Geigy Corporation, Ardsley, N.Y.

[21] Appl. No.: 784,410

[22] Filed: Apr. 4, 1977

Related U.S. Application Data

[63] Continuation of Ser. No. 561,526, Mar. 24, 1975, abandoned, which is a continuation-in-part of Ser. No. 330,526, Feb. 8, 1973, abandoned.

[30] Foreign Application Priority Data

Feb. 9, 1972 [CH] Switzerland .......................... 1870/72
Jan. 12, 1973 [CH] Switzerland ............................ 438/73

[51] Int. Cl.² ............................................. C07C 43/22
[52] U.S. Cl. .................................. 568/636; 424/341; 568/637; 568/638; 568/586; 568/639
[58] Field of Search ......................... 260/613 R, 612 D

[56] References Cited

U.S. PATENT DOCUMENTS 3,340,308 9/1967 Sterling et al. ................... 260/613 R

FOREIGN PATENT DOCUMENTS 795129 8/1973 Belgium.
1510861 12/1967 France.

OTHER PUBLICATIONS

Fellig et al., Jour. Agr. Food Chem., vol. 18 (1970) 78–80.

Primary Examiner—Bernard Helfin
Attorney, Agent, or Firm—Harry Falber

[57] ABSTRACT

Compounds of the formula

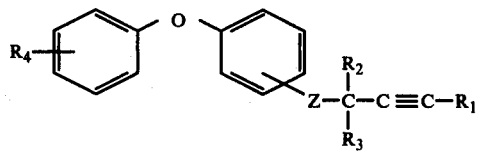

wherein
$R_1$ represents hydrogen, methyl or iodine,
$R_2$ represents hydrogen, methyl or ethyl
$R_3$ represents hydrogen or methyl
$R_4$ represents hydrogen, $C_1$–$C_3$ alkyl; $C_1$–$C_3$ alkoxy; halogen or nitro, and
Z represents oxygen, or the group —$CH_2O$—, whereby the $CH_2$-group is bound to the phenyl nucleus, and their use for the control of insects are disclosed.

4 Claims, No Drawings

PHENOXYPHENYL- AND PHENOXYBENZYL-ALKYNYL ETHERS

CROSS REFERENCE

This is a continuation of application Ser. No. 561,526 filed on Mar. 24, 1975, which in turn, is a continuation-in-part of application Ser. No. 330,526, filed Feb. 8, 1973, both now abandoned.

The present invention relates to phenyl- and benzyl-alkynyl ethers, to their production, and to their use for the control of insects.

The compounds correspond to the formula

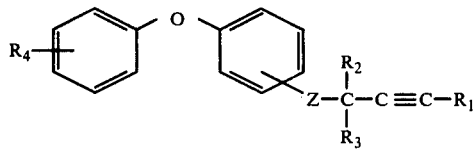

wherein
$R_1$ represents hydrogen, methyl or iodine,
$R_2$ represents hydrogen, methyl or ethyl,
$R_3$ represents hydrogen or methyl,
$R_4$ represents hydrogen, $C_1$–$C_3$alkyl; $C_1$–$C_3$alkoxy; halogen or nitro, and
Z represents oxygen, or the group —$CH_2O$—, whereby the $CH_2$-group is bound to the phenyl nucleus.

Compounds to be particularly emphasised because of their effectiveness are compounds of formula I wherein
$R_1$ represents hydrogen, methyl or iodine,
$R_2$ represents hydrogen or methyl,
$R_3$ represents hydrogen,
$R_4$ represents hydrogen, methyl, ethyl, ethoxy, chlorine or nitro and
Z represents oxygen, or the group —$CH_2O$—, whereby the $CH_2$-group is bound to the phenyl nucleus.

The production of the compounds of formula I is effected in a manner known per se (e.g. according to Houben-Weyl, Vol. VI/3, pp. 10-40, 1965) by the following reactions:

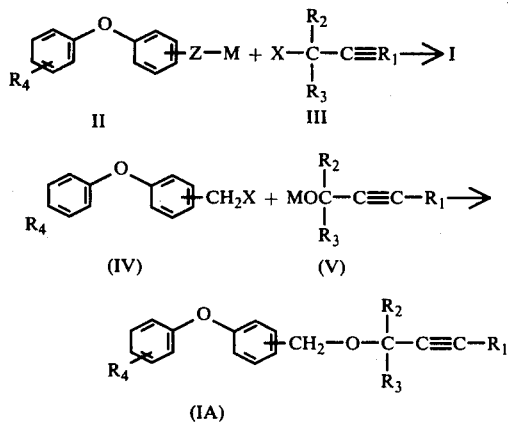

In the formulae II, III, IV and V, the symbols $R_1$, $R_2$, $R_4$ and Z have the meanings given for formula I, M stands for a cation, preferably a metal, particularly for a metal of the I. or II. main group of the periodic system, or for hydrogen, and X stands for halogen, preferably chlorine, bromine or iodine.

The compounds of formula I can be obtained by reaction of a compound of formula II with an alkynyl halide of formula III in various solvents and at various reaction temperatures.

Suitable inert solvents are especially ketones, such as, e.g. acetone, methyl ethyl ketone, isopropyl-methyl ketone, cyclohexanone, also dimethoxyethane, tetrahydrofuran, dioxane, dialkyl ether, dimethylformamide, dimethylsulphoxide, hexamethylphosphoric acid triamide, or hydrocarbons such as toluene, xylene or benzene.

Bases are used for the production of the alcoholate or phenolate of formula II. Suitable bases or acid acceptors are, in particular, alkali and alkaline-earth carbonates, alkali and alkaline-earth hydroxides, alkali or alkaline-earth hydrides and alkali alkoxides. With the use of alkali or alkaline-earth hydrides, alkali or alkaline-earth hydroxides or alkali alkoxides as bases, the phenol or the alcohol can firstly be converted in a suitable solvent into the alkali or alkaline-earth phenolate or alcoholate (formula II, M = alkali or alkaline-earth metal); the alkynyl halide is then allowed to act on the thus formed phenolate or alcoholate.

Alkali or alkaline-earth carbonates as acid acceptors are preferably added direct to the reaction mixture consisting of phenol II, alkynyl halide III and inert solvent. Preferred solvents with the employment of alkali and alkaline-earth carbonates as bases are ketones, e.g. acetone, methyl ethyl ketone, isopropyl methyl ketone or cyclohexanone. Particularly preferred in this group of acid acceptors is potassium carbonate.

The reaction temperatures for the ether formation are between 0° and ca. 120° C., preferably between room temperature and 80° C., or, e.g. the boiling temperature of the applied solvent (acetone, methyl ethyl ketone, etc.).

The compounds of formula I wherein Z represents the group —$CH_2O$— can also be obtained by reaction of a halide of formula IV with an alcoholate of formula V, in the presence of a solvent, at various reaction temperatures. Suitable solvents are ethers such as, e.g. tetrahydrofuran, dioxane, dialkyl ether, 1,2-dimethoxyethane, also dimethylformamide, dimethylsulphoxide, hexamethylphosphoric acid triamide, or hydrocarbons such as toluene, benzene or xylene.

The reaction temperatures are between −10° and 100° C., preferably between 0° and 70° C.

Bases used for the production of the alcoholate of formula V are, in particular, alkali alkoxides and alkali hydrides.

The preparation and isolation of compounds of formula I are effected by known techniques; e.g., by a process in which the reaction solution is filtered off from the solid substance on the bottom, the filtrate concentrated by evaporation, the residue taken up in a suitable solvent (e.g. ether, hexane), and this solution washed with dilute alkali solution and water. After the drying of the organic phase over sodium sulphate and removal of the solvent, the obtained alkynyl ether of formula I can, if necessary, be further purified by crystallisation, high vacuum distillation, or chromatography on silica gel or aluminium oxide. The reaction mixture can, moreover, be poured on ice or into ice water and subsequently extracted with a suitable solvent (e.g. ether, methylene chloride, hexane). The further isolation and purification of the reaction product is then as described above.

The starting materials of formulae II, III, IV and V are known compounds, or can be produced by methods analogous to known methods described in the literature. The compounds of formula I are suitable for the control of insects. To be particularly emphasised is the larvicidal and ovicidal action of the compounds of formula I against insects, e.g. of the following orders and families:

| | |
|---|---|
| Orthopetra | Acrididae |
| | Gryllidae |
| | Blattidae |
| Isoptera | Kalotermitidae |
| Hemiptera | Miridae |
| | Piesmidae |
| | Lygaeidae |
| | Pyrrhocoridae |
| | Pentatomidae |
| | Cimicidae |
| | Reduviidae |
| | Jassidae |
| | Eriosomatidae |
| | Lexaniidae |
| Coleoptera | Carabidae |
| | Elateridae |
| | Coccinellidae |
| | Tenebrionidae |
| | Dermestidae |
| | Cucujidae |
| | Chrysomelidae |
| | Curculionidae |
| | Scolytidae |
| | Scarabaeidae |
| Lepidoptera | Pyralidae |
| | Phyticidae |
| | Pyraustidae |
| | Crambidae |
| | Tortricidae |
| | Galleriidae |
| | Lyonetiidae |
| | Yponomeutidae |
| | Pieridae |
| | Plutellidae |
| | Lymantriidae |
| | Noctuidae |
| Piptera | Culicidae |
| | Simuliidae |
| | Tipulidae |

In the French Pat. No. 1,510,861 and in the German 'Offenlegungsschriften' Nos. 2,049,391 and 2,100,325, analogous compounds are described as synergists to known insecticides.

Surprisingly, it has now been found that the compounds of formula I have an appreciably better action against larvae and eggs of insects than that of the known compounds.

First and foremost is the action of the compounds of formula I against mosquito larvae.

The compounds of formula I can be used on their own or together with suitable carriers and/or additives. Suitable carriers and additives can be solid or liquid and they correspond to substances common in formulation practice, such as, e.g. natural or regenerated substances, solvents, dispersing agents, wetting agents, adhesives, thickeners, bonding agents and/or fertilisers. For application, the compounds of formula I can be processed into the form of dusts, emulsion concentrates, granulates, dispersions, sprays or solutions, the formulation of the said preparations being effected in a manner commonly known in practice.

The agents according to the invention are produced in a manner known per se by the intimate mixing and/or grinding of active substances of formula I with suitable carriers, optionally with the addition of dispersing agents or solvents which are inert to the active substances. The active substances can be obtained and used in the following preparation forms:

Solid forms:

Dusts, scattering agents, granules, coated granules, impregnated granules and homogeneous granules.

Liquid forms:

(a) active substances which are dispersible in water: wetting powders, pastes, emulsions;
(b) solutions.

To manufacture solid forms (dusts, scattering agents), the active substances are mixed with solid carriers. Suitable carriers are, for example: kaolin, talcum, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

Granules can be very easily manufactured by dissolving an active substance of the formula I in an organic solvent and applying the resulting solution to a granulated material, for example attapulgite, $SiO_2$, granicalcium, bentonite etc. and then evaporating the solvent.

Polymer granules can also be manufactured by mixing the active substances of the formula I with polymerisable compounds (urea/formaldehyde; dicyandiamide/formaldehyde; melamine/formaldehyde or others), whereupon a mild polymerisation carried out that does not affect the active substances and in the process of which the granulation is carried out during the gel formation. It is more advantageous to impregnate finished, porous polymer granules (urea/formaldehyde, polyacrylonitrile, polyester or others) which have a specific surface area and a favourable predeterminable adsorption/desorption ratio, with the active substances, for example in the form of their solutions (in a low boiling solvent) and to remove the solvent. Polymer granules of this kind in the form of microgranules having a bulk density of 300 g/liter to 600 g/liter can also be manufactured with the aid of atomisers. The dusting can be carried out from aircraft over extensive areas of cultures of useful plants.

It is also possible to obtain granules by compacting the carrier with the active substance and carriers and subsequently comminuting the product.

To these mixtures can also be added additives which stabilise the active substance and/or non-ionic, anionic and cationic surface active substances, which, for example, improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (Carbowax), fatty alcohol polyethylene glycol ethers having 5 to 20 ethylene oxide radicals per molecule and 8 to 18 carbon atoms in the fatty alcohol moiety, condensation products of ethylene oxide/propylene oxide, polyvinyl pyrrolidones, polyvinyl alcohols, condensation products of urea and formaldehyde, and also latex products.

The water-dispersible concentrates of the active substance, i.e. wettable powders, pastes and emulsifiable concentrates, are agents which can be diluted with water to any concentration desired. They consist of active substance, carrier, optionally additives which stabilise the active substance, surface-active substance and anti-foam agents and optionally, solvents.

Wettable powders and pastes are obtained by mixing and grinding the active substances with dispersing agents and pulverulent carriers in suitable apparatus until homogeneity is attained. Suitable carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metals salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl ethionate, the sodium salts of oleoyl methyl tauride, ditertiary acetylene glycols, dialkyl dilauryl ammonium chloride and fatty acid alkali and alkaline earth metal salts.

Suitable anti-foams agents are silicones.

The active substance are mixed, ground, sieved and strained with the additives cited hereinabove in such a manner that, the size of the solid particles does not exceed 0.02 to 0.04$\mu$ in wettable powders, and 0.03$\mu$ in pastes. To produce emulsifiable concentrates and pastes, dispersing agents such as those cited above, organic solvents, and water are used. Examples of suitable solvents are: alcohols, benzene, xylene, toluene, dimethyl sulphoxide, and mineral oil fractions which boil between 120° and 350° C. The solvents must be practically odourless, not phytotoxic, and inert to the active substances.

Furthermore, the agents according to the invention can be applied in the form of solutions. For this purpose the active substances, or several active substances of the general formula I, are dissolved in suitable organic solvents or in water. Aliphatic and aromatic hydrocarbons, chlorinated derivatives thereof, alkyl naphthalenes and mineral oils, singly or in admixture with each other, can be used as organic solvents.

The content of active substance in the above described agents is between 0.1% to 95%, in which connection it should be mentioned that, in the case of application from aircraft or some other suitable means of application, it is possible to use concentrations of up to 99.5% or even pure active substance.

The active substances of the formula I can, for example, be formulated as follows:

Dusts

The following substances are used to manufacture (a) a 5% and (b) a 2% dust:

(a)
  5 parts of active substance
  95 parts of talcum
(b)
  2 parts of active substance
  1 part of highly disperse silicic acid
  97 parts of talcum.

The active substances are mixed with the carriers and ground.

Granules

The following substances are used to produce 5% granules:
  5 parts of active substance,
  0.25 parts of epichlorohydrin,
  0.25 parts of cetyl polyglycol ehter,
  3.50 parts of polyethylene glycol,
  91 parts of kaolin (particle size 0.3–0.8mm).

The active substance is mixed with epichlorohydrin and dissolved with 6 parts of acetone: the polyethylene glycol and cetyl polyghlycol ether are then added. The thus obtained solution is sprayed on kaolin, and the acetone subsequently evaporated in vacuo.

Wettable powder

The following constituents are used for the preparation of (a) a 40%, (b) and (c) a 25%, and (d) a 10% wettable powder:

(a)
  40 parts of active substance,
  5 parts of sodium lignin sulphonate,
  1 part of sodium dibutyl-naphthalene sulphonate,
  54 parts of silicic acid.
(b)
  25 parts of active substance,
  4.5 parts of calcium lignin sulphonate,
  1.9 parts of Champagne chalk/hydroxyethyl cellulose mixture (1:1),
  1.5 parts of sodium dibutyl naphthalene sulphonate,
  19.5 parts of silicic acid,
  19.5 parts of Champagne chalk,
  28.1 parts of kaolin.
(c)
  25 parts of active substance,
  2.5 parts of isooctylphenoxy-polyoxyethyleneethanol,
  1.7 parts of Champagne chalk/hydroxyethyl cellulose mixture (1:1),
  8.3 parts of sodium aluminium silicate,
  16.5 parts of kieselguhr,
  46 parts of kaolin.
(d)
  10 parts of active substance,
  3 parts of a mixture of the sodium salts of saturated fatty alcohol sulphates,
  5 parts of naphthalenesulphonic acid/formaldehyde, condensate,
  82 parts of kaolin.

The active substances are intimately mixed, in suitable mixers, with the additives, the mixture being then ground in the appropriate mills and rollers. Wettable powders are obtained which can be diluted with water to give suspension of any desired concentration.

Emulsifiable concentrates

The following substance are used to produce (a) a 10% (b) a 25% emulsifiable and (c) a 50% emulsifiable concentrate:

(a)
- 10 parts of active substance,
- 3.4 parts of epoxidised vegetable oil,
- 13.4 parts of combination emulsifier consisting of fatty alcohol polyglycol ether and alkylarylsulphonate calcium salt,
- 40 parts of dimethylformamide,
- 43.2 parts of xylene.

(b)
- 25 parts of active substance,
- 2.5 parts of epoxidised vegetable oil,
- 10 parts of an alkylarylsulphonate/fatty alcoholpolyglycol ether mixture
- 5 parts of dimethylformamide,
- 57.5 parts of xylene.

(c)
- 50 parts of active substance,
- 4.2 parts of tributylphenol-polyghylkolether,
- 5.8 parts of calcium-dodecylbenzolsulphonate,
- 20 parts of cyclohexanon,
- 20 parts of xylole.

From these concentrates it is possible to produce, by dilution with water, emulsions of any desired concentration.

Spray

The following constituents are used to prepare (a) a 5% and (b) a 95% spray:

(a)
- 5 parts of active substance,
- 1 part of epichlorohydrin,
- 94 parts of benzine (boiling limits 160°–190° C.).

(b)
- 95 parts of active substance,
- 5 parts of epichlorohydrin,

EXAMPLE 1

A mixture of 18.6 g of 4-hydroxy-diphenyl ether, 13.1 g of propargyl bromide and 16.6 g of anhydrous potassium carbonate in 150 ml of acetone is stirred for 16 hours at the reflux temperature. The reaction mixture is thereupon filtered off from the substance on the bottom, the acetone distilled off in vacuo, and the oily residue taken up in 200 ml of ether/hexane (1:1); this solution is washed four times with 10% potassium hydroxide solution and subsequently with water until neutral. The organic phase is finally dried over sodium sulphate and filtration performed. After the solvent and the volatile fractions have been completely removed in vacuo from the filtrate, there is obtained analytically pure 4-propargyloxydiphenyl ether; $n_D^{20}$: 1.5830.

EXAMPLE 2

An amount of 5.2 g of a ca. 60% suspension of sodium hydride in mineral oil is washed twice with hexane and once with tetrahydrofuran, and finally suspended in 40 ml of tetrahydrofuran. An addition is then made dropwise within half an hour, with slight cooling, of 7.4 g of propargyl alcohol, and stirring continued for a further 3 hours at room temperature. After the formation of the alcoholate, there is added dropwise, in the course of ca. one hour, the solution of 26.3 g of 4-bromomethyldiphenyl ether in 40 ml of hexamethylphosphoric acid triamide and 10 ml of tetrahydrofuran, and the whole further stirred overnight at room temperature. To effect the isolation of the product, the reaction mixture is poured into ca. 500 ml of ice water, and extraction repeatedly performed with diethyl ether. The combined ether phases are successively washed, until neutral, with water, 10% potassium hydroxide solution, and finally with sodium chloride solution. After the drying of the ether solution over sodium sulphate, the solvent and the volatile fractions are completely removed in vacuo, and the oil-like 4-propargyloxymethylene-diphenyl ether remaining behind further purified by chromatography on silica gel (eluant: diethyl ether/hexane 1:4); $n_D^{20}$: 1.5710.

Also the following compounds are produced in an analogous manner to that described in Examples 1 and 2.

| Active Substance | Physical data |
|---|---|
| 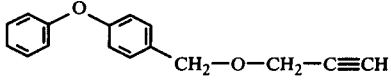 | $n_D^{20}$:1,5710 |
| 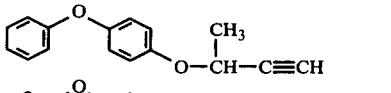 | M.P.:53–54° C. |
| 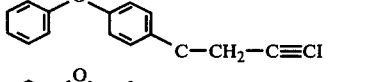 | M.P.:59–60° C. |
| 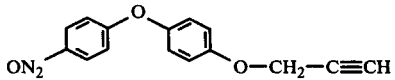 | $n_D^{20}$:1,5699 |
| 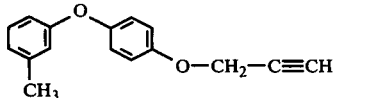 | M.P.:57–58° C. |
| 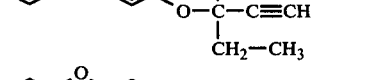 | $n_D^{20}$:1,5821 |
| 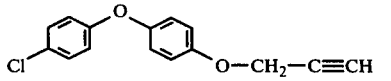 | $n_D^{20}$:1,5185 |
| 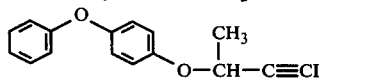 | $n_D^{20}$:1,5812 |
| 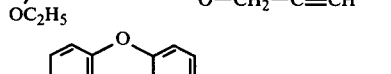 | M.P.:38–39° C. |
| | $n_D^{20}$:1,5759 |
| | M.P:61–62° C. |
| | M.P.:53–54° C. |
| | M.P.:38–39° C. |

| Active Substance | Physical data |
|---|---|
| -continued | |
| 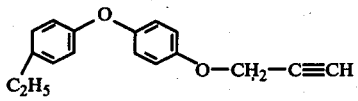 | $n_D^{20}: 1.5700$ |

EXAMPLE 3

Inhibitory effect on larvae of *Dysdercus fasciatus*

Ten larvae of *Dysdercus fasciatus*, which were 8–10 days before moulting into the adult stage, were topically treated with acetonic active-substance solutions. The larvae were then kept at 28° C. with 80–90% relative humidity; they were fed on the shred of presoaked cottonseed. After ca. 10 days, i.e. as soon as the test insects had completed moulting, the insects were examined to determine the number of normal adults. The compounds according to Examples 1 to 3 exhibited a high degree of effectiveness in the above test.

EXAMPLE 4

Inhibitory effect in the gas phase on the eggs of *Spodoptera littoralis*

Into one 130 ml flask with ground glass stopper were placed 40 mg of active substance, and into another of 175 ml content 100 eggs of *Spodoptera littoralis*. The two flasks were connected with a connecting member, and maintained at 25° C.

The evaluation of the inhibitory effect was made after 5 to 6 days.

Compounds according to Examples 1 to 3 displayed a high degree of effectiveness in the above test.

EXAMPLE 5

Into a beaker containing a solution of active substance (concentration 5 ppm) were placed about twenty 2-day-old larvae of the yellow fever mosquito (*Aedes aegypti*). The beaker was then covered with a perforated lid. After the test-insects had completed their moult into the adult stage, the insects were examined and the percentage of normal adults determined, taking as a basis the number of normal adults present in the control test.

The compounds according to Examples 1 to 3 exhibited a high degree of effectiveness in the above test.

I claim:
1. 1-Propargyloxy-4-phenoxy-benzene.
2. 3-[(4-phenoxy)-phenoxy]-1-iodo-1-propyne.
3. 1-Propargyloxy-4-(4-ethyl-phenoxy)-benzene.
4. 1-Propargyloxy-4-(2-methylphenoxy)benzene.